United States Patent
Chiang

[19]

[11] Patent Number: 6,032,298
[45] Date of Patent: Mar. 7, 2000

[54] SWIMMING GOGGLE STRUCTURE

[76] Inventor: Herman Chiang, 11F, No. 634-9, Ching-Ping Rd., Chung-Ho City, Taipei Hsien, Taiwan

[21] Appl. No.: 08/873,441

[22] Filed: Jun. 12, 1997

[51] Int. Cl.[7] .................................................... A61F 9/02
[52] U.S. Cl. .................................................. 2/428; 2/443
[58] Field of Search ............................. 2/428, 429, 430, 2/440, 441, 442, 443, 439, 445, 452, 426

[56]           References Cited

U.S. PATENT DOCUMENTS

| | | | |
|---|---|---|---|
| 1,565,890 | 12/1925 | Baker | 2/441 X |
| 3,122,962 | 3/1964 | DeAngelis | 2/441 |
| 3,259,909 | 7/1966 | Wood | 2/440 |
| 5,046,198 | 9/1991 | Hannebeck | 2/440 |

*Primary Examiner*—Peter Nerbun

*Attorney, Agent, or Firm*—Pro-Techtor Int'l Srevices

[57]           ABSTRACT

A swimming goggle structure includes two frames, each having a lens seat defined by a raised wall formed thereon to support a lens. A loop-like lens securing member, is removably fit onto the raised wall of the frame to hold the lens on the lens seat of the frame. The raised wall has an inner surface on which a sideways-opened groove for supporting and holding the lens is provided and an outer side on which a circumferential shoulder is formed to support the loop-like lens securing member. The shoulder has a lateral groove recessed into and Co-extensive with the raised wall and the loop-like lens securing member has a corresponding inward-projecting rib receivable within the outer groove of the circumferential shoulder to removably hold the lens securing member on the lens seat so as to allow a user to replace the lens by oneself by removing the lens securing member from the raised wall of the frame.

12 Claims, 10 Drawing Sheets

SWIMMING GOGGLE STRUCTURE

FIELD OF THE INVENTION

Thy present invention is related generally to swimming goggles and in particular to a swirling goggle structure which allows a wearer to change the lenses.

BACKGROUND OF THE INVENTION

Figure 1:
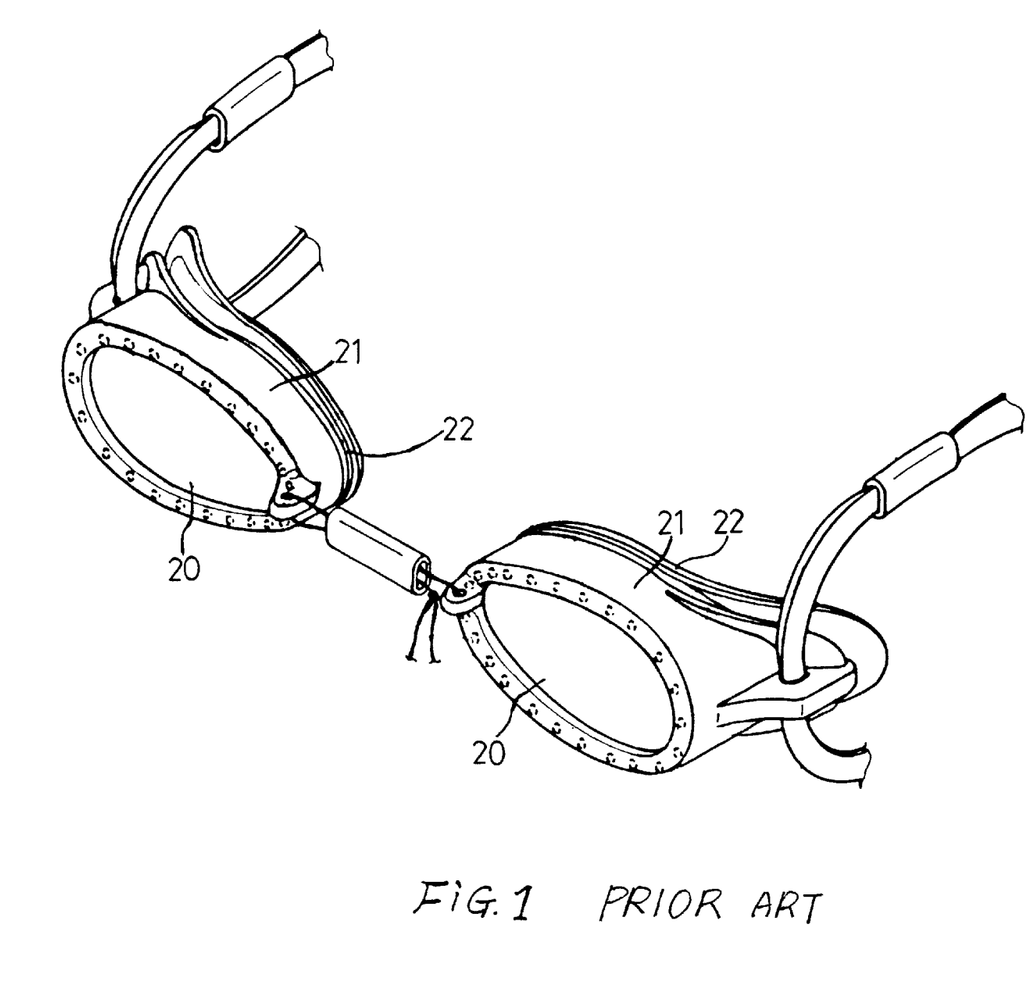
FIG. 1 is a perspective view showing a conventional swimming goggle structure wherein the lenses are separate members from the frames.

Based on the way how the lens is mounted on the frame of swimming goggles, the swimming goggles may be classified into two groups, one of which is that the lenses are separate member and not integrally formed on the frame, such as U.S. Pat. Nos. 1,742,412, 2,150,791 and U.S. Pat. No. 5,524,300. The other kind of swimming goggles is that the lenses are integrally mounted on the frames to form a single piece. An example of the swimming goggles having separate lenses is illustrated in FIG. 1 of the attached drawings, wherein the frames 21 and the cushion pads 22 are injection molded together and the lenses 20 are then mounted to the frames 21.

Figure 2:
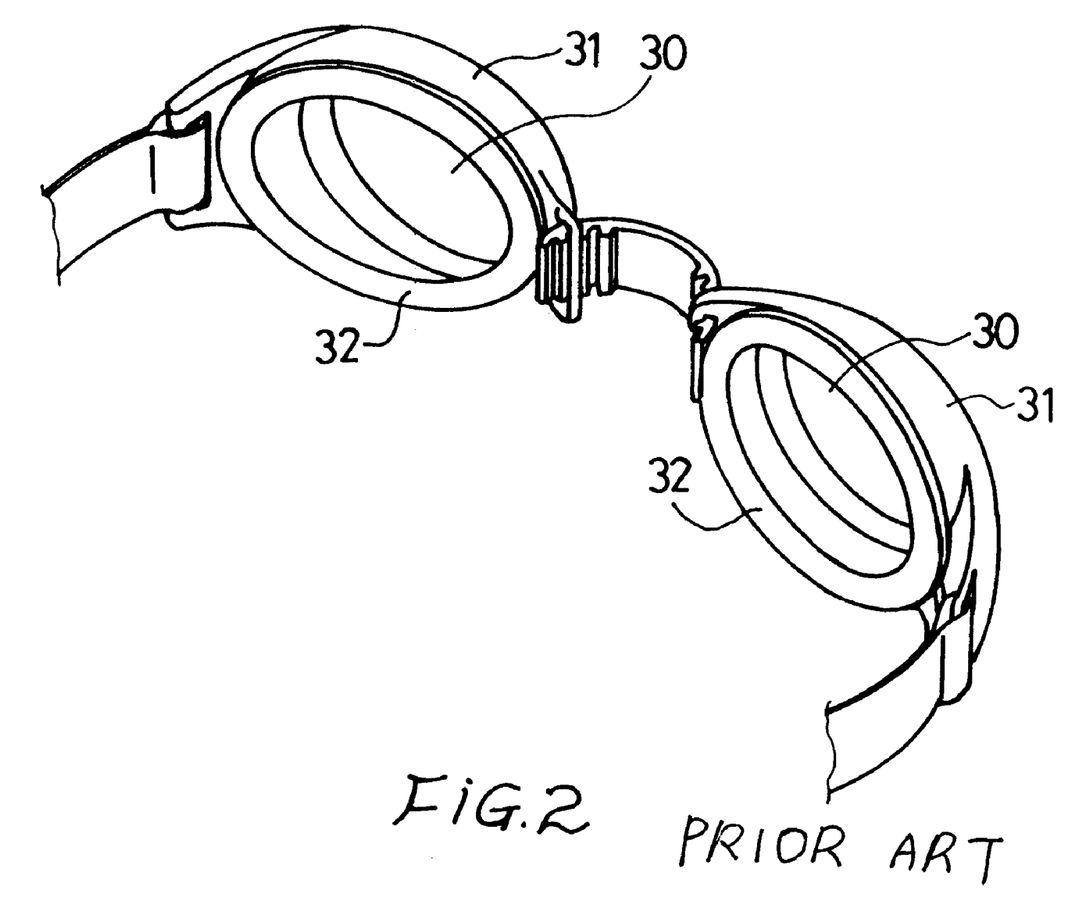
FIG. 2 is a perspective view showing a conventional swimming goggle structure therein the lenses are integrally formed with the frames.

FIG. 2 shows an example of the single piece swimming goggle structure in which the lenses 30 are integrally formed on the frames 31 and then the cushion pads 32 are adhered to the frames 31. Both designs of the swimming goggles have advantages and disadvantages. However, among the disadvantages, there is a drawback common to both designs. Namely, once the lenses are worn out or broken, the swimming goggles are totally useless and have to be replaced by a new pair.

Further, for use in an outdoor swimming pool, to protect the wearer's eyes, the lenses are usually colored in order to partially block intense sun light. But for those used in an indoor swimming pool, such colored lenses may not be suitable and instead, clear lenses are used. It is of course not likely for a user or consumer to have two pairs of swimming goggles to be respectively used in indoor and outdoor swimming pools. This is both inconvenient and costly.

It it thus desirable to provide a swimming goggle structure which allows a user to change the lenses by oneself so as to overcome the above-mentioned drawback.

SUMMARY OF THE INVENTION

Therefore, a primary object of the present invention is to provide a swimming goggle structure wherein the lenses are separate from the frames and user-exchangeable so that a user may selectively mount different lenses on the frames of the swimming goggles.

To, achieve the above object, there is provided a swimming goggle structure wherein the frame comprises a lens seat formed thereon to support a lens. The lens seat is in the form of a circumferential raised wall along the frame. A loop-like lens securing member, is then removably fit onto the raised wall of the frame to hold the lens on the lens seat of the frame. The lens seat that is formed as a raised wall along the frame has an inner surface on which a sideways-opened groove having a top wall for supporting and holding the inner side edge of the lens is provided and an outer side on which a circumferential shoulder or step is formed to support the loop-like lens securing member. The shoulder has a lateral groove recessed into and co-extensive with the raised wall of the lens seat. The loop-like lens securing member comprises a corresponding projection receivable within the outer groove of the circumferential shoulder to be fixed on the raised wall.

In accordance with another aspect of the present invention, the loop-like lens securing member is cut off at a predetermined position to form a slit so as to define an open loop for readily mounting to the raised wall of the frame. A gap may be present at the cut of the loop-like lens securing member when the loop-like lens securing member is fit over the raised wall of the frame. A boss is integrally formed with the loop at the cut and is also separated into two sections along the cut so as to be spaced from each other by the gap. A fastening device is provided to fasten the two sections of the boss together so as to secure the lens securing member on the raised wall.

Further, in accordance with the present invention, the fastening device comprises a cap having an interior space with a partition member formed therein corresponding to the gap between the two sections of the boss so that when the loop-like lens securing member is fit over the raised wall and the cap fit over the boss, the partition member is inserted into the gap between the two sections of the boss to guide the cap to be fit over and thus hold the two sections of the boss together to secure the loop on the raised wall of the frame.

In accordance with the present invention, preferably, the partition member is tapering to define a thinner free end for ready insertion into the gap and to guide the cap to fit over the boss.

Further, to more securely hold the lens on the frame, the groove that is formed on the outer shoulder and recessed into the raised wall is preferably located below the inner step of the raised wall so that when the projection of the loop-like lens securing member is fit therein, the projection of the loop-like lens securing member forces the material of the raised wall inward and deform the inner step to more tightly abut against the inner side of the lens, which in combination with a pressure applied on the outer side of the lens by means of an abutting edge of the loop-like lens securing member, securely holds the lens on the frame.

The object, advantages and features of the present invention will be apparent from the following description of preferred embodiments, with reference to the attached drawings, wherein;

DETAILED DESCRIPTION OF THE PREFERRED EMBODIMENTS

Figure 3:
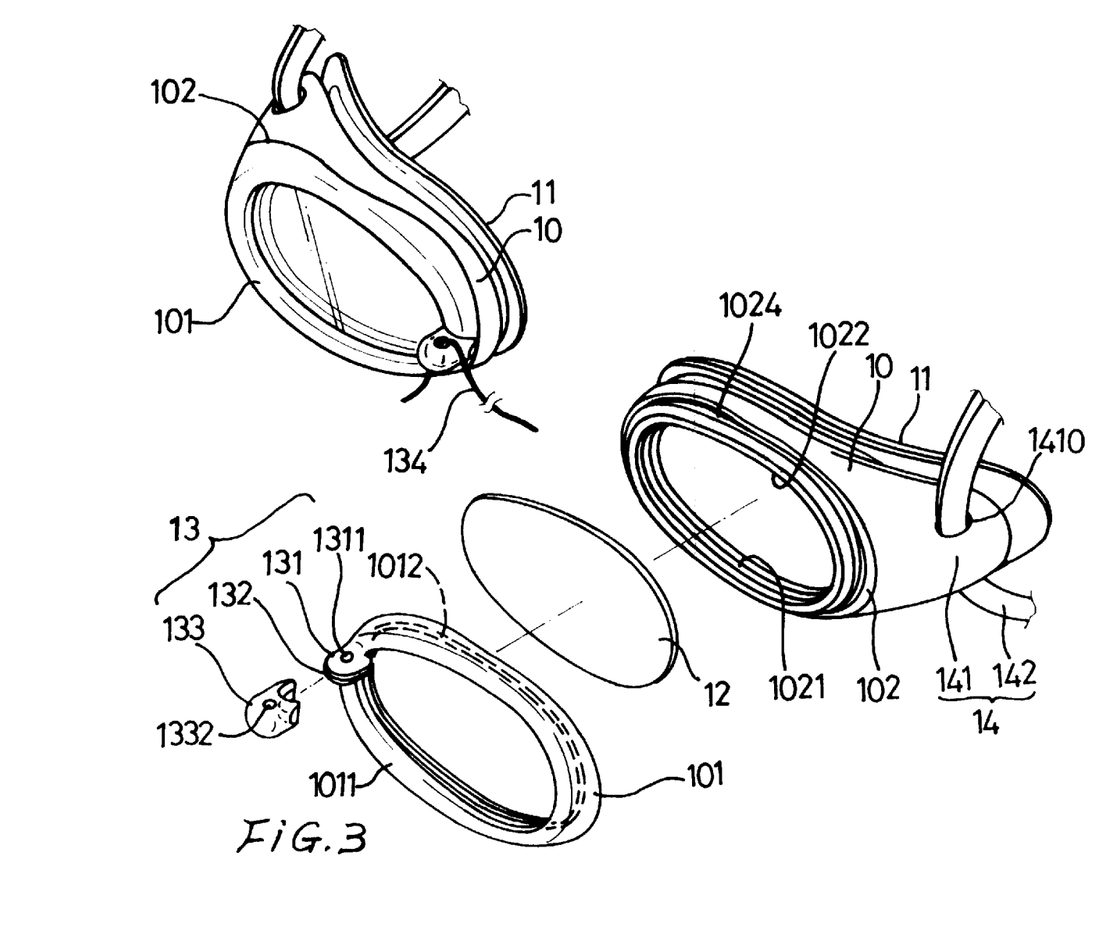
FIG. 3 is an exploded perspective view showing a swimming goggle structure in accordance with the present invention having exchangeable lenses.

Referring to the drawings and in particular to FIG. 3, wherein a swimming goggle structure in accordance with the present invention, generally designated at 1, is shown, the swimming goggle structure shown in FIG. 3 is the type which comprises two separate frame 10, each having a cushion pad 11 integrally formed thereon. Each of the frames 10 defines therein a receiving bore or a lens seat for receiving therein a lens 12. A loop-like lens securing member 101, is provided to mount to the lens seat and hold the lens 12 therein. The swimming goggles 1 further comprise fastening means 13 for fastening the lens securing loop 101 to securely hold the lens 12 in the respective frame 10. Also, head strap means 14 is provided for mounting the swimming goggles 1 on a wearer's head (not shown).

The frames 10 and respective cushion pads 11 are made of resilient material by means of injection molding to be a single piece. At the right hand side of FIG. 3, the lens 12 is shown separated from the frame 10. As shown, the frame 10 has a circumferential raised wall, which defines the lens seat, formed thereon and extends along the frame 10. The lens seat that is defined by the raised wall comprises the receiving bore for receiving the lens 12 therein. The lens seat has an inner groove 1021, hating a circumferential top side wall 1022, formed inside the raised wall of the frame 10 and along the receiving bore to receive and support a circumferentrial edge of the inner side of the lens 12 and an outer shoulder 102 located outside the raised wall and extending along the frame 10. The top side wall 1022 of the groove 1021 serves to more securely hold the lens 12 therein. The loop-like lens securing member 101 is fit over the raised wall to hold the lens 12 in position. The raised wall of the frame 10 has first engaging means formed thereon and correspondingly, the loop-like lens securing member 101 comprises second engaging means engageable with the first engaging means for holding the lens securing member 101 on the frame 10.

The first engaging means comprise a groove 1024 formed on the circumferential shoulder 102, recessed into the raised wall and extending around the frame 10. The lens securing loop 101 has an L- or J-shaped cross section having a short section and a long section with an inner abutting edge 1011 formed at the short section to correspond to and abut against the top side wall 1022 of the inner groove 1021 and an inward-projecting rib 1012 on the long section which defines the second engaging means receivable within the groove (the first engaging means) 1024 so as to fix the lens securing loop 101 on the raised wall of the frame 10 to secure the lens 12 in position.

Referring to the left hand side of FIG. 3, which shows the completely assembled, condition of the frame 10 and the lens 12. It is shown that the lens securing loop 101 is mounted on the raised wall with the long section seated on the outer shoulder 102 (FIGS. 5A and 5B), the rib 1012 received within the outer groove 1024, and the abutting edge 1011 of the securing loop 101 engaging the top side wall 1022 of the inner groove 1021. The securing loop 101 is sized and configured to provide a smooth outer surface with the frame 10 when it is fit over the raised wall.

The fastening means 13 comprises a boss 131 which is preferably integrally formed with the securing loop 101 and located corresponding to the nose bridge of the swimming goggles. A slit 132 extends through the boss 131 to the lens securing loop 101 to separate the boss into two separate sections and also cut off the lens securing loop 101 to define two free ends thereof, thus allowing the two sections of the boss 131 to be movable relative to each other. With such a slit 132, a gap may be present between the two sections of the post 131 (the two free ends of the lens securing loop 101) when the lens securing loop 101 is fit over the raised wall of the frame 10. This helps mounting the lens securing loop 101 to the raised wall of the frame 10.

The boss 131 is provided with a hole or passage 1311 through which for example a rope 134 or other adjustable connecting piece for connecting the two frames 10 to each other may extend.

A cop 133 is sized and configured to be fit over the boss 131. The cap 133 comprises a hollow interior having an open bottom with a partition member 1331 formed therein, see FIG. 6. Preferably the partition member 1331 is tapering toward the bottom opening of the cap 133 and corresponding to the slit 132 of the boss 131 so that when the cap 133 is fit over the boss 131, the partition member 1331 is inserted into the slit 132 in order to guide the cap 133 to fit over the boss 131. Fitting tho,cap 133 over the two separate sections of the boss 131 of the securing loop 101 fastens the two sections of the boss 131 together and thus effectively secures the securing loop 101 on the frame 10. The cap 131 may be provided with through holes 1332 in registration with the passage 1311 of the boss 131 to allow the rope 134 to extend therethrough.

Figure 6:
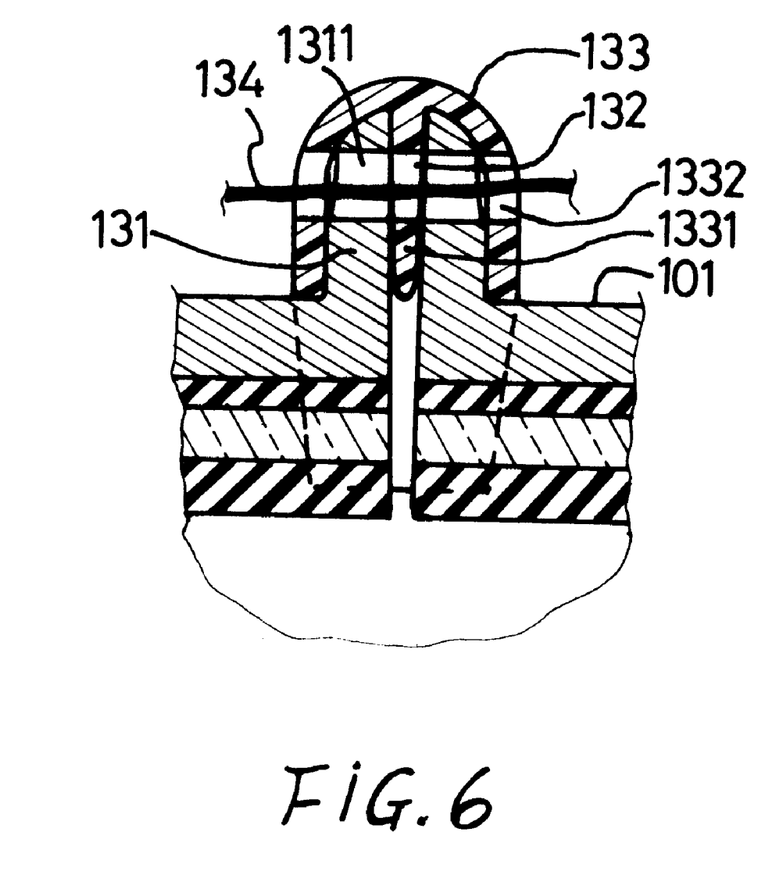
FIG. 6 is a cross-sectional view of a portion of the lens securing member, showing the two sections of the boss are fastened by the fastening cap.

The partition member 1331 inside the cap 133 divides the interior space of the cap into two sub-spaces, each having a cross section widened toward the bottom opening to be readily fit over the respective section of the boss 131.

In the embodiment illustrated, the head strap means 14 comprises a strap holder 141 and a strap 142. The strap holder 141 is integrally formed on the frame 10, defining a channel 1410 on the frame 10 through which the strap 142 extends. The strap 142 may be a rope or a rubber strip which extends through the channel 1410 and is tightened thereon. If desired, an adjustable member (not shown) may be provided on for example the rubber strip to adjust the length thereof.

Figure 4:
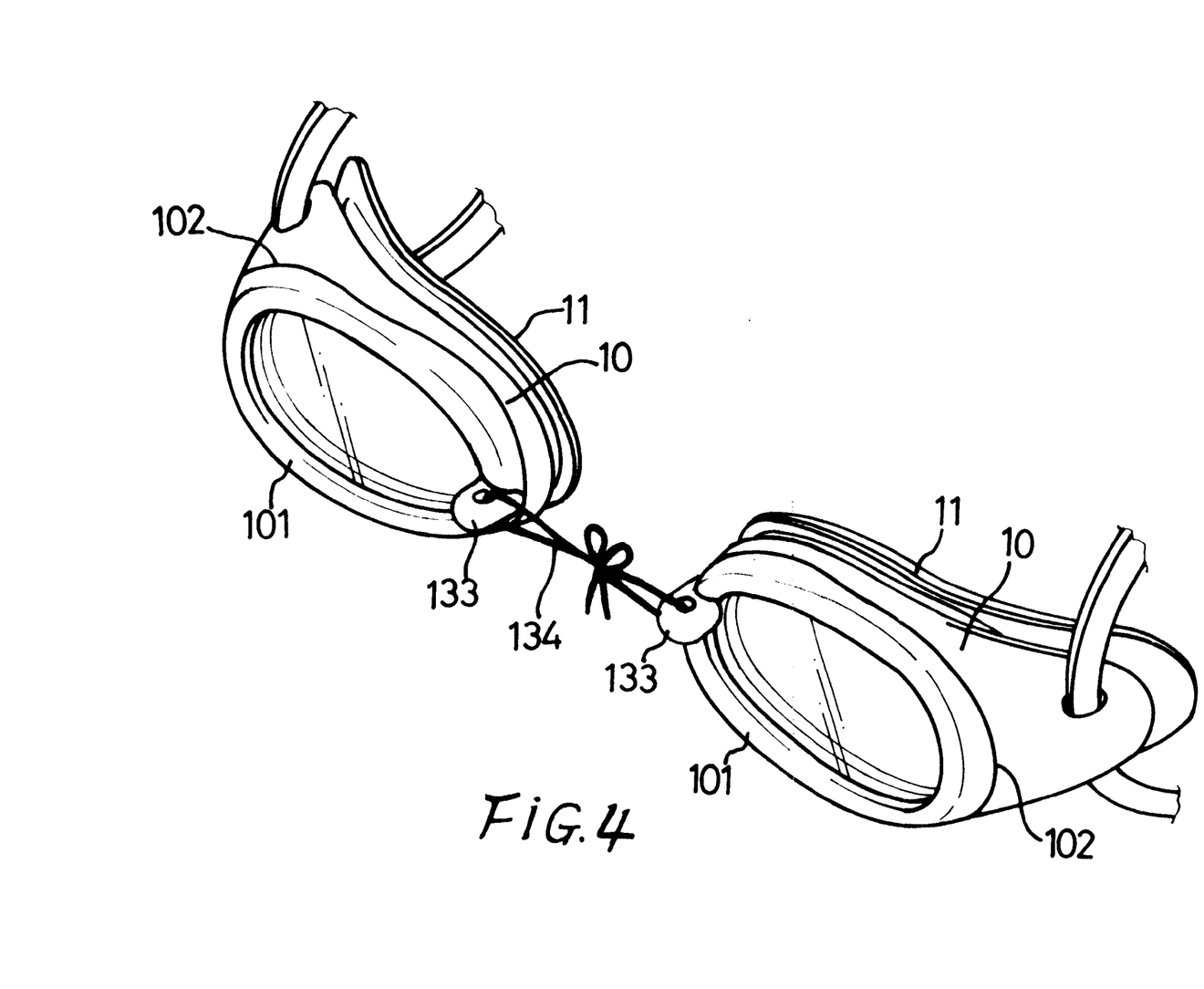
FIG. 4 is a perspective view of the swimming goggles of the present invention.

FIG. 4 shows the completely assembled swimming goggles in which the securing loops 101 of both the two frames 10 are mounted to secure the lenses 12 on the frames 10. The two frames 10, together with the securing loops 101 and the lenses 12, are tightened to each other by means of the rope 134 extending through the holes 1311 of the bosses 131 of the securing loops 101. Each of the frames 10 has a cushion pad 11 integrally formed thereon for comfortable compliance with the wearer's face (not shown).

Figure 5A:
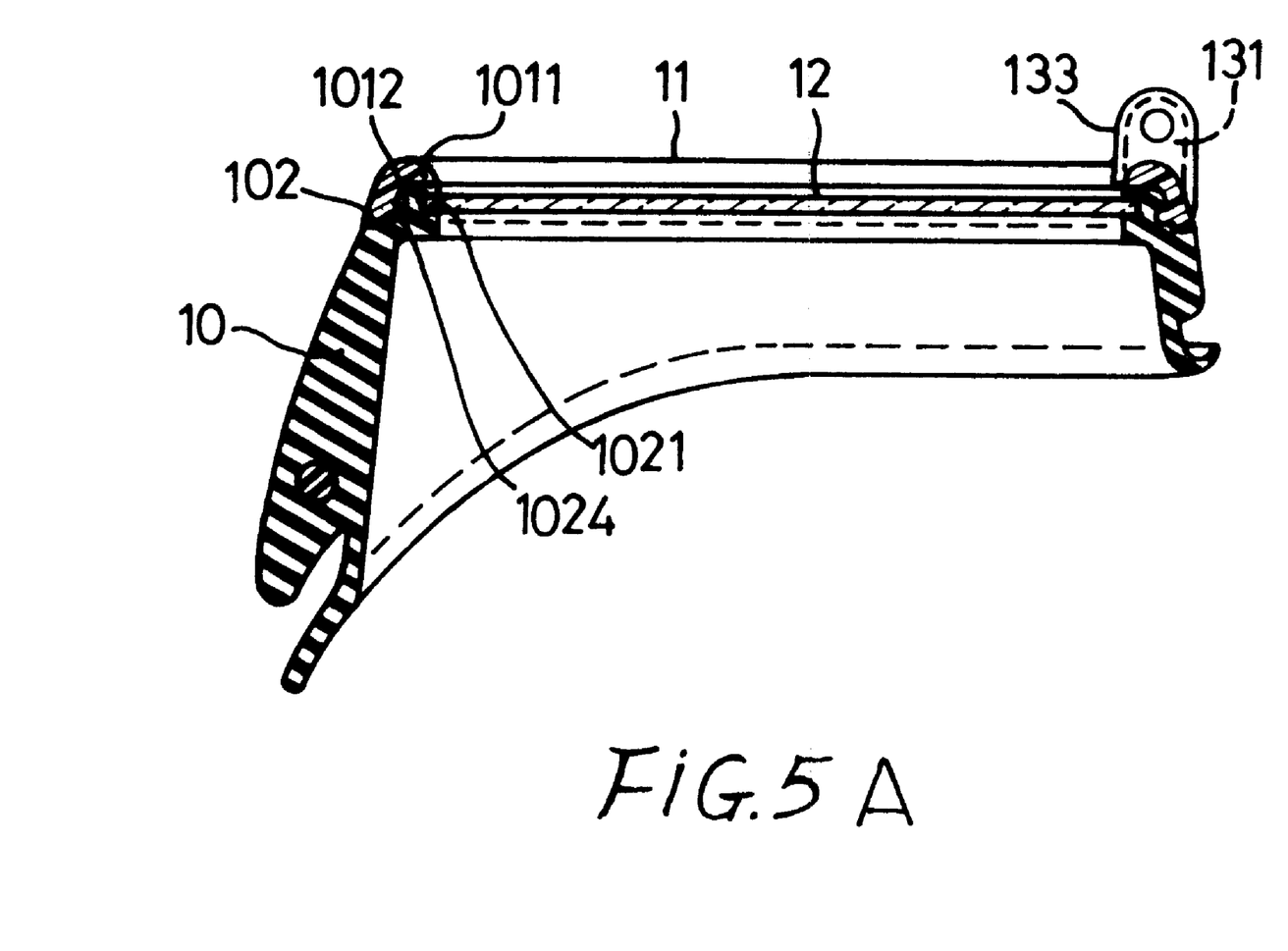
FIG. 5A is a cross-sectional view of a portion of the swimming goggles of the present invention with the lens fixed on the frame by the lens securing member.
Figure 5B:
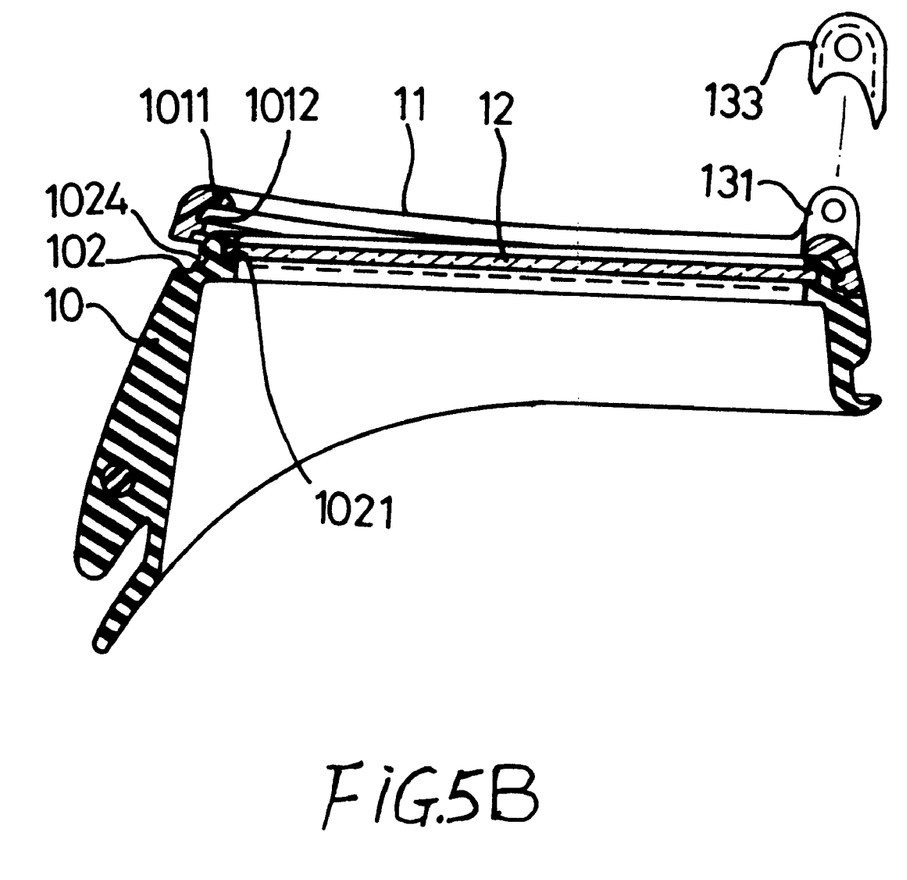
FIG. 5B is a cross-sectional view similar to FIG. 5A, but with the lens securing member released.

The relationship between the lens securing loop 101 and the outer shoulder 102 of the frame 10 is illustrated in FIGS. 5A and 5B. As shown, by arranging the outer groove 1024 to be located below the inner groove 1021, when securing loop 101 is mounted to the frame 10 to have the rib 1012 fit into the outer groove 1024, the force that applies from the rib 1012 of the securing loop 101 to the frame 10 in securing the loop 101 forces the material of the raised wall inward and thus deform the inner groove 1021 to act on and more tightly abut against the inner side of the lens 12, while, the abutting edge 101 1 of the securing loop 101 abuts against the outer side of the lens 12 so as to securely hold the lens 12 within the frame 10. Fitting the cap 133 onto the boss 131 further helps the securing loop 101 to securely hold the lens 12, as shown in FIG. 5A.

If it is desired to change the lens 12, then the securing loop 101 is released from the frame 10 by using one hand to hold the cap 133 and using the other hand to depress the outer edge of the frame 10, as indicated by the arrow of FIG. 5A. By doing so, the rib 1012 is disengaged from the outer groove 1024, as shown in FIG. 5B. The lens 12 may then be readily removed from the frame 10 and a new lens is mounted into the frame 10. In assembling the lens 12 and the securing loop 101, the operation is completely reversed, namely, with the lens supported and held in the inner groove 1021, positioning the long section of the securing loop 101 on the shoulder 102 at one side only and then fitting the securing loop 101 over the raised wall by forcibly pressing long section of the securing loop 101 onto the shoulder 102 at the opposite side.

Figure 7:
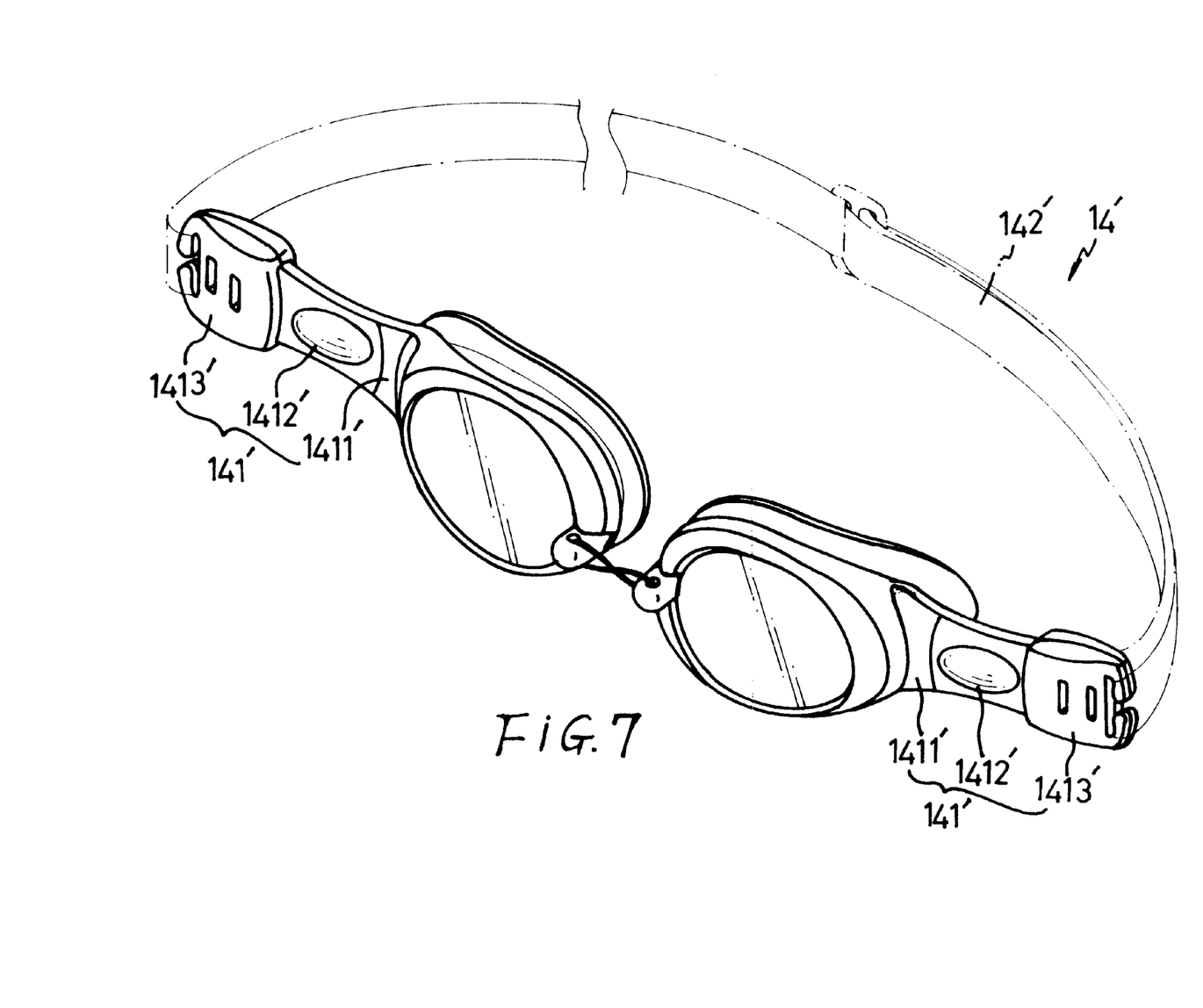
FIG. 7 is a perspective view showing a pair of swimming goggles constructed in accordance with a second embodiment of the present invention.

With reference to FIG. 7, which shows a pair of swimming goggles in accordance with a second embodiment of the present invention. The second embodiment swimming goggle structure is similar to the first embodiment with the only exception in that the structure of the head strap means is changed, which is designated with reference numeral 14' for distinction. The head strap means 14' of the second embodiment comprises an anti-stretching section 141', a strap 142' and an adjustable buckle 143'. The anti-stretching section 141' comprises a front portion 1411', a middle portion 1412' and a rear portion 1413'. The rear portion 1413' comprises a connector for connecting the head strap. The front portion 1411' and middle portion 1412' are formed with successive or single recess (pit) to provide a better anti-stretching effect.

Figure 8:
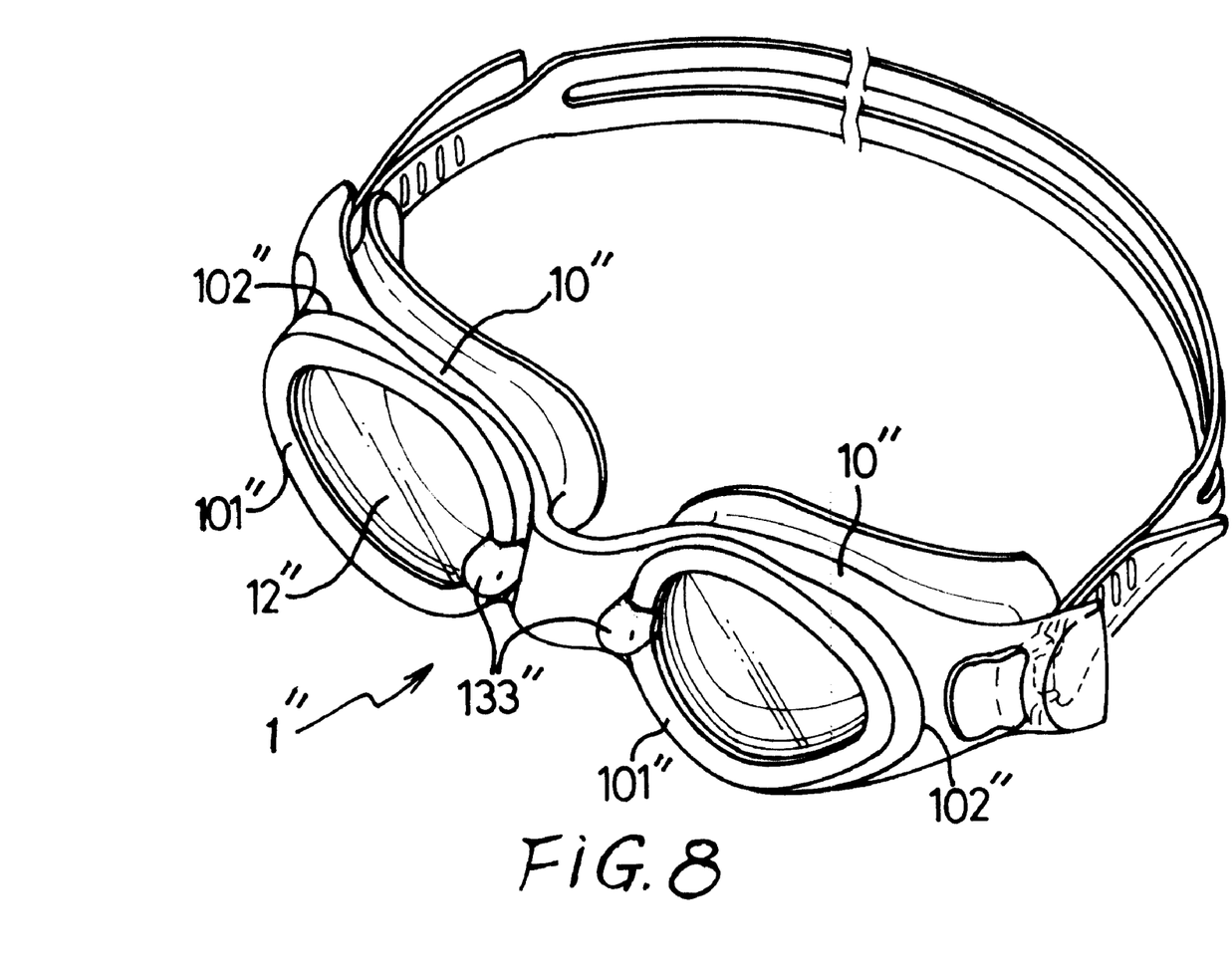
FIG. 8 is a perspective view showing a pair of swimming goggles constructed in accordance with a third embodiment of the present invention.

With reference to FIG. 8, which shows the application of the present invention in a swimming goggle structure in which the frames, the bridge and the cushion pads are integrally formed with each other, the swimming goggle structure 1" illustrated in the embodiment of FIG. 8 comprises two frames 10", each having a lens 12" mounted thereon and fixed by a securing loop 101" which is fit over the raised wall of the frame 10" and supported on the circumferential shoulder 102" and fastened by a cap 133" fit thereon to securely hold the lenses 12" in the frames 10".

Figure 9:
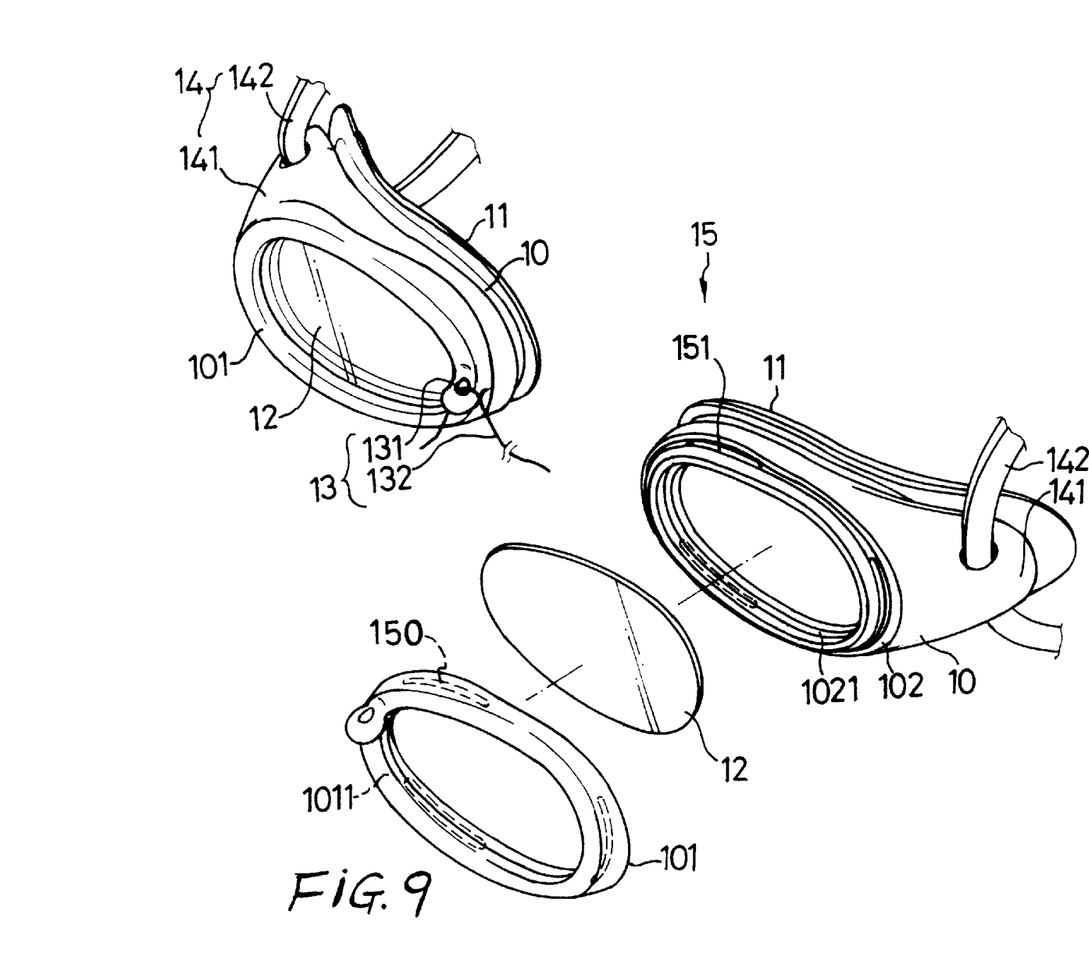
FIG. 9 is a perspective view showing a pair of swimming goggles constructed in accordance with a fourth embodiment of the present invention.

FIG. 9 shows a pair of swimming goggles constructed in accordance with a fourth embodiment of the present invention which is different from the first embodiment in that no fastening means 13 is needed in the fourth embodiment and the securing loop 101' is fixed to the shoulder 102' by means of projection-slot pairs. As shown, the swimming goggle structure of the fourth embodiment also comprises cushion 4' ads 11' integrally formed on the frame 10' and lenses 12' supported and held within the frames 10', a bridge 13' connecting between the two frames 10' and head strap means 14' for mounting the swimming goggles on a wearer's head (not shown) and loop fastening means 15' for fastening the securing loop 101' on the frame 10', wherein the frames 10', the cushion pads 11', the lenses 12', the bridge 13' and the head strap means 14' are all similar to the counterparts of first embodiment so that further discussion is not needed. However, the loop fastening means 15' which secures the securing loop 101' on the frame 10' is different. With reference to FIG. 9, the frame ' 10' comprises a raised wall Co.-extensive therewith, defining an inner groove 1021' for supporting a circumferential edge of the lens 12'. The securing loop 101' comprises an abutting edge 1011' which is to abut against the edge of the lens 12'. The fastening means 15' is provided between the securing loop 101' and the outside shoulder 102' and comprises a plurality of separate projections or ribs 150' provided inside the securing loop 101' and a plurality of corresponding slots 151' formed on the outer shoulder 102' and recessed into the raised wall. The projections 150' are spaced from each other along the securing loop 101'. The slots 151' are formed on the shoulder 102' to be sized and positioned corresponding to the ribs 150' for receiving and holding the ribs 150 therein so as to secure the securing loop 101' to the frame 10' and thus fixing the lens 12' on the inner groove 1021' of the raised ' wall of the frame 10'. With reference to the left side of drawing 9, which shows a completely assembled condition of the fourth embodiment swimming goggles. It is preferable that the securing loop 101' which is mounted on the raised wall of the frame 10' provides a smooth and continuous outside surface of the swimming goggle frame.

The above description is made with respect to the preferred embodiments of the present intention and for those skilled in the art, it is possible to made a variety of modifications and changes to the above-described specific embodiments without departing from the scope and spirit of the present invention. All these modifications and changes should be considered within the scope of the present invention as defined hin the appended claims.

What is claimed is:

1. A swimming goggle structure comprising:

two frames connected to each other by a connecting piece, each of the frames comprising a raised wall co-extensive therewith, having an inner surface defining thereon lens support means and an outer surface defining thereon first engaging means;

a lens received within each of the frames and having a circumferential edge supported on the lens support means formed on the inner surface of the raised wall;

a loop-like lens securing member comprising a first section having an abutting edge and a second section having second engaging means engageable with the first engaging means to removably hold the loop-like lens securing member on the raised wall of the frame with the abutting edge abutting against the lens supported on inner step; and head strap means adapted to mount the swimming goggle structure to a wearer's head; wherein the lens support means comprises a circumferential recess opened sideways and extending along the frame to receive the second section of the lens securing means therein, the recess defining a top side wall to more securely hold the second section of the lens securing means therein, the first engaging means is provided on the outer surface of the raised wall at a location below the lens support means formed on the inner surface of the raised wall, the first engaging means comprises a groove extending along the raised wall and recessed into the outer surface of the raised wall and wherein the second engaging means comprises an inward-projecting rib formed along the loop-like lens securing member to be receivable within the recessed groove on the outer surface of the raised wall, the loop-like lens securing member comprises fastening means which comprises a slit cut through a cross section of the lens securing member to define two opposite free ends, each having a raised section mounted thereon to be movable relative to each other for facilitating mounting the lens securing member to the raised wall of the frame and a cap which is removably fit over both the raised sections so as to fasten the two separate raised sections together, a gap is present between the free ends defined at the slit of the lens securing member when the lens securing member is fit over the raised wall, and the cap comprises an interior space having an open bottom to be fit over the two raised sections of the lens securing member, a partition member being provided inside the cap to be corresponding to the gap and being tapered toward the bottom opening for insertion into the gap.

2. The swimming goggle structure as claimed in claim 1, wherein the partition member of cap divide the interior space of the cap into two sub-spaces, each having a gradually widened cross-section toward the bottom opening.

3. The swimming goggle structure as claimed in claim 2, wherein a passage extends through the fastening cap and the two raised sections of the lens securing member through which the connecting piece that connects the two frames extends.

4. The swimming goggle structure as claimed in claim 3, wherein each of the frames is provided with anti-stretching means to be coupled with by the head strap means.

5. A lens frame of swimming goggles, adapted to removably hold therein a lens, the frame comprising a lens seat for receiving therein the lens and a loop-like lens securing member removably engageable with the lens seat to hold the lens in position, the lens seat comprising a raised wall formed on and co-extensive with the frame, having an inner surface defining thereon lens support means for supporting a circumferential edge of the lens and an outer surface defining thereon first engaging means, the loon-like lens securing member comprising a first section having an abutting edge received within an inner surface of the raised wall to abut against the lens and a second section fit over the outer surface of the raised wall and having second engaging means engageable with the first engaging means to removably hold the loop-like lens securing member on the raised wall of the frame; wherein the lens support means comprises a circumferential recess having a circumferential top side wall extending along the frame to receive the first section of the lens securing means, the first engaging means is provided on the outer surface of the raised wall at a location below the lens support means formed on the inner surface of the raised wall, the first engaging means comprises a groove extending along the raised wall and recessed into the outer surface of the raised wall and wherein the second engaging means comprises an inward-projecting rib formed along the loop-like lens securing member to be receivable within the recessed groove on the outer surface of the raised wall, and the loop-like lens securing member comprises fastening means which comprises a slit cut through a cross section of the lens securing member to define two opposite free ends, each having a raised section mounted thereon to be movable relative to each other for facilitating mounting the lens securing member to the raised wall of the frame and a cap which is removably fit over both the raised sections of the lens securing member so as to fasten the two separate raised sections together.

6. The lens frame as claimed in claim 5, wherein a gap is present between the free ends defined at the slit of the lens securing member when the lens securing member is fit over the raised wall.

7. The lens frame as claimed in claim 6, wherein the cap comprises an interior space having an open bottom to be fit over the two raised sections of the lens securing member, a partition member being provided inside the cap to correspond to the gap and being tapering toward the bottom opening for insertion into the gap.

8. The lens frame as claimed in claim 7, wherein the partition member of the cap divides the interior space of the cap into two sub-spaces, each having a gradually widened cross-section toward the bottom opening.

9. The lens frame as claimed in claim 8, wherein the frame further comprises anti-stretching means mounted on an outside surface thereof.

10. The lens frame as claimed in claim 9, wherein a passage extends through the fastening cap and the two raised sections of the lens securing member through which a connecting piece that connects the flames to a second frame extends.

11. The lens frame as claimed in claim 9, wherein the frame further comprises a nose bridge section.

12. The lens frame as claimed in claim 11, wherein the nose bridge section is integrally formed on the frame.

* * * * *